United States Patent [19]

Clark et al.

[11] Patent Number: 5,974,389
[45] Date of Patent: Oct. 26, 1999

[54] MEDICAL RECORD MANAGEMENT SYSTEM AND PROCESS WITH IMPROVED WORKFLOW FEATURES

[76] Inventors: Melanie Ann Clark; John Finley Gold; Michael Edward Huska; Geoffrey Harold Kabel; Marc Merrill Graham, all of c/o Glaxo Wellcome Inc., Five Moore Dr., Research Triangle Park, N.C. 27709

[21] Appl. No.: 08/609,844

[22] Filed: Mar. 1, 1996

[51] Int. Cl.⁶ .................................................. G06F 17/60
[52] U.S. Cl. ...................................... 705/3; 707/8
[58] Field of Search .............................. 364/400; 705/2, 705/3; 707/8

[56] References Cited

U.S. PATENT DOCUMENTS

| | | | |
|---|---|---|---|
| 3,656,687 | 4/1972 | Romney et al. | 234/2 |
| 3,970,996 | 7/1976 | Yasaka et al. | 340/172.5 |
| 4,116,470 | 9/1978 | Johnsen | 283/66 |
| 4,121,574 | 10/1978 | Lester | 128/2.05 |
| 4,130,881 | 12/1978 | Haessler et al. | 364/900 |
| 4,159,129 | 6/1979 | Lockhart | 282/27 |
| 4,221,404 | 9/1980 | Shuffstall | 283/1 |
| 4,228,506 | 10/1980 | Ripley et al. | 364/415 |
| 4,277,089 | 7/1981 | Lockhart | 282/27 |
| 4,290,114 | 9/1981 | Sinay | 364/900 |
| 4,370,983 | 2/1983 | Lichtenstein | 128/630 |

(List continued on next page.)

OTHER PUBLICATIONS

Naeymi–Rad, Frank, et al., *IMR–Entry (Intelligent Medical Record–Entry*, AMIA, Inc., 1993, pp. 783–384.

*Electronic Medical Record System Supports 800 Simultaneous Users*, Cerner News Release, Feb. 14, 1995.

*Performance Analysis*, Cerner Corporation, Aug. 5, 1994, pp. 3–6.

Trace, David, et al., *Intelligent Medical Record–Entry (IMR–E)*, Journal of Medical Systems, vol. 17, Mar. 4, 1993, pp. 139–151.

Naeymi–Rad, Frank, et al., *Informatics Workup*, 16th Annual Symposium in Computer Applications in Medical Care, AMIA, Inc., 1993, pp. 545–549.

Ma, H., et al., *A Productive User Environment for Generating Progress Notes*, undated.

Trace, D., et al., *Medical Information Management: The Medas Approach*, undated.

Rifat, Sami, et al., *MEDRIS: The Problem Oriented Electronic Medical Record in Medical Education*, undated.

Ma, H., et al., *An Interactive System for Generating Hospital Progress Notes*, undated.

Naeymi–Rad, Frank, et al., *Steps in Implementing a Multiuser Integrated Electronic Medical Record*, MEDINFO 92, 1992, pp. 724–729.

Naeymirad, Shon, et al., *The Portable Patient File: An Intelligent Automated Medical Record*, undated.

Trace, David, et al., *A Longitudinal Medical Record (IMR)*, AMIA, Inc., 1994.

Carmony, Lowell, et al., *Knowledge Generation Via a Simple Grammar Supporting an Intelligent User Interface*, 12th Annual Symposium on Computer Applications in Medical Care, Nov. 6–9, 1988, pp. 136–140.

Trace, David, et al., *MEDAS: The Integrated Approach to Medical Information Management*, undated.

Robert, Shanthi, et al., *Hypercard Front End for a Medical Expert System*, undated.

Robert, Shanthi, et al., *Collecting Patient Data Using a Hypermedia–Based Clinical System*, undated.

*Primary Examiner*—Edward R. Cosimano
*Attorney, Agent, or Firm*—Charles E. Dadswell

[57] ABSTRACT

A patient medical record system includes a number of caregiver computers, and a patient record database with patient data coupled to the caregiver computers selectively providing access to the patient data from one of the caregiver computers responsive to a predetermined set of access rules. The predetermined set of rules includes a rule that access to a predetermined portion of the patient data by a first caregiver must be terminated before access to the same predetermined portion by a second caregiver is allowed.

14 Claims, 3 Drawing Sheets

U.S. PATENT DOCUMENTS

| | | | |
|---|---|---|---|
| 4,464,172 | 8/1984 | Lichtenstein | 604/65 |
| 4,489,387 | 12/1984 | Lamb et al. | 364/514 |
| 4,533,221 | 8/1985 | Trachtman | 351/203 |
| 4,572,891 | 2/1986 | Drexler | 430/346 |
| 4,622,013 | 11/1986 | Cerchio | 434/118 |
| 4,625,276 | 11/1986 | Benton et al. | 364/408 |
| 4,665,004 | 5/1987 | Drexler | 430/140 |
| 4,667,292 | 5/1987 | Mohlenbrock et al. | 364/406 |
| 4,792,968 | 12/1988 | Katz | 379/92 |
| 4,799,712 | 1/1989 | Biava et al. | 282/1 |
| 4,835,372 | 5/1989 | Gombrich et al. | 235/375 |
| 4,845,739 | 7/1989 | Katz | 379/92 |
| 4,850,009 | 7/1989 | Zook et al. | 379/96 |
| 4,855,842 | 8/1989 | Hayes et al. | 358/342 |
| 4,857,713 | 8/1989 | Brown | 235/375 |
| 4,857,716 | 8/1989 | Gombrich et al. | 235/462 |
| 4,858,121 | 8/1989 | Barber et al. | 364/406 |
| 4,869,531 | 9/1989 | Rees | 283/67 |
| 4,878,175 | 10/1989 | Norden-Paul et al. | 364/413.01 |
| 4,893,270 | 1/1990 | Beck et al. | 364/900 |
| 4,916,441 | 4/1990 | Gombrich | 340/712 |
| 4,918,572 | 4/1990 | Tarver et al. | 361/395 |
| 4,939,508 | 7/1990 | Lawrence et al. | 340/710 |
| 4,945,476 | 7/1990 | Bodick et al. | 364/413.02 |
| 4,945,477 | 7/1990 | Edwards | 364/413.06 |
| 4,974,607 | 12/1990 | Miwa | 128/904 |
| 4,975,842 | 12/1990 | Darrow et al. | 364/413.02 |
| 5,006,699 | 4/1991 | Felkner et al. | 235/472 |
| 5,016,172 | 5/1991 | Dessertine | 364/413.02 |
| 5,018,067 | 5/1991 | Mohlenbrock et al. | 364/413.02 |
| 5,019,976 | 5/1991 | Chiu et al. | 364/413.13 |
| 5,025,374 | 6/1991 | Roizen et al. | 364/413.02 |
| 5,048,075 | 9/1991 | Katz | 379/92 |
| 5,054,096 | 10/1991 | Beizer | 382/41 |
| 5,065,315 | 11/1991 | Garcia | 364/413.01 |
| 5,067,834 | 11/1991 | Szmanda et al. | 400/489 |
| 5,070,452 | 12/1991 | Doyle, Jr. et al. | 364/401 |
| 5,072,383 | 12/1991 | Brimm et al. | 364/413.02 |
| 5,077,666 | 12/1991 | Brimm et al. | 364/413.02 |
| 5,099,424 | 3/1992 | Schneiderman | 364/413.02 |
| 5,101,476 | 3/1992 | Kukla | 395/200 |
| 5,121,470 | 6/1992 | Trautman | 395/140 |
| 5,133,045 | 7/1992 | Gaither et al. | 395/51 |
| 5,136,502 | 8/1992 | Van Remortel et al. | 364/413.01 |
| 5,140,519 | 8/1992 | Friesdorf et al. | 364/413.03 |
| 5,146,562 | 9/1992 | Kukla | 395/200 |
| 5,148,366 | 9/1992 | Buchanan et al. | 364/419 |
| 5,193,855 | 3/1993 | Shamos | 283/117 |
| 5,208,907 | 5/1993 | Shelton et al. | 395/149 |
| 5,225,976 | 7/1993 | Tawil | 364/401 |
| 5,235,510 | 8/1993 | Yamada et al. | 364/413.02 |
| 5,235,702 | 8/1993 | Miller | 395/600 |
| 5,247,611 | 9/1993 | Norden-Paul et al. | 395/161 |
| 5,253,164 | 10/1993 | Holloway et al. | 364/406 |
| 5,253,361 | 10/1993 | Thurman et al. | 395/600 |
| 5,253,362 | 10/1993 | Nolan et al. | 395/600 |
| 5,255,309 | 10/1993 | Katz | 379/88 |
| 5,259,023 | 11/1993 | Katz | 379/88 |
| 5,262,943 | 11/1993 | Thibado et al. | 364/413.01 |
| 5,265,010 | 11/1993 | Evans-Paganelli et al. | 364/413.02 |
| 5,267,155 | 11/1993 | Buchanan et al. | 364/419.14 |
| 5,272,625 | 12/1993 | Nishihara et al. | 364/413.13 |
| 5,274,749 | 12/1993 | Evans | 395/63 |
| 5,276,612 | 1/1994 | Selker | 364/413.06 |
| 5,276,805 | 1/1994 | Hamaguchi | 395/164 |
| 5,277,188 | 1/1994 | Selker | 128/696 |
| 5,287,414 | 2/1994 | Foster | 382/1 |
| 5,287,459 | 2/1994 | Gniewek | 395/275 |
| 5,291,399 | 3/1994 | Chaco | 364/413.02 |
| 5,292,029 | 3/1994 | Pearson | 221/2 |
| 5,296,688 | 3/1994 | Hamilton et al. | 235/375 |
| 5,297,216 | 3/1994 | Sklarew | 382/13 |
| 5,301,319 | 4/1994 | Thurman et al. | 395/600 |
| 5,305,748 | 4/1994 | Wilk | 128/653.1 |
| 5,307,262 | 4/1994 | Ertel | 364/413.01 |
| 5,307,263 | 4/1994 | Brown | 364/413.09 |
| 5,315,505 | 5/1994 | Pratt et al. | 364/413.01 |
| 5,319,543 | 6/1994 | Wilhelm | 364/401 |
| 5,324,077 | 6/1994 | Kessler et al. | 283/54 |
| 5,325,293 | 6/1994 | Dorne | 364/413.01 |
| 5,325,294 | 6/1994 | Keene | 364/413.01 |
| 5,325,478 | 6/1994 | Shelton et al. | 395/148 |
| 5,325,523 | 6/1994 | Beglin et al. | 395/600 |
| 5,327,341 | 7/1994 | Whalen et al. | 364/413.01 |
| 5,331,549 | 7/1994 | Crawford, Jr. | 364/413.02 |
| 5,493,724 | 2/1996 | Cohn et al. | 395/858 |
| 5,546,580 | 8/1996 | Seliger et al. | 707/8 |
| 5,594,638 | 1/1997 | Iliff | 705/3 |
| 5,606,679 | 2/1997 | Cohn et al. | 711/4 |
| 5,721,943 | 2/1998 | Johnson | 706/59 |
| 5,742,813 | 4/1998 | Kavanagh et al. | 707/8 |

MEDICAL RECORD MANAGEMENT SYSTEM AND PROCESS WITH IMPROVED WORKFLOW FEATURES

37C.F.R.1.71 AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office records, but otherwise reserves all copyright rights whatsoever.

BACKGROUND OF THE INVENTION

This invention relates generally to systems and methods of clinical information management and specifically to systems and processes by which electronic medical records may be maintained in an environment in which a patient encounter may involve multiple caregivers and in which a caregiver may have need to simultaneously access information for multiple patients.

The literature is replete with references to systems for maintaining electronic patient records. Such electronic records are touted as possible replacements for traditional paper patient records, permitting faster access to patient information, search capabilities, and facilities for immediate transmission of information from caregivers in one location (e.g., an attending physician's office) to another location (e.g., a hospital emergency room).

As medical records become ever more detailed and complex, the need for automated processes for collecting, storing, transmitting, and retrieving patient medical information becomes more critical. Historically, hand-entered medical records were very brief and were sometimes of limited value for future care, either because entries were illegible, used non-standard abbreviations, lacked sufficient detail, or were difficult to search. It has been widely reported in the literature that such difficulties resulted in negative effects on clinical judgment, patient care plans, medical record audits, medical education, and physician performance evaluation.

Early attempts at providing automated patient records typically used codes to represent a diagnosis or problem, with additional detail being provided in narrative form. These first-generation systems provided some advantages over traditional hard-copy records, but were never widely adopted by the medical community. It has been speculated that such systems never provided the practical ease of use required to convince caregivers to switch from paper-based records.

One example of a more advanced electronic patient record system was MEDAS, or Medical Emergency Decision Assistance System. MEDAS was developed starting in the 1970s at the University of Southern California and then at the University of Health Sciences/The Chicago Medical School. MEDAS included features for the capture of patient history, physical examination, and chief complaint information.

Another system, MEDRIS, or Medical Record Input System, employed a hypermedia approach to capture patient history and physical examination data. MEDRIS sought to guide physicians through the particular tasks used for these encounters, and also permitted the collection of data from other types of encounters, such as brief drop-in visits.

As smaller desktop computers, as, well as notebook computers and pen-based computers, became widely available, attention turned to multi-user systems to permit a network of caregivers to store and access patient information. One such system integrated MEDAS with an Intelligent Medical Record Entry module for data entry and also provided a portable patient file.

Despite the various advantages they provide over paper-based records, even current-generation systems have not enjoyed widespread acceptance by the medical profession. It is believed that a number of practical factors continue to limit the use of electronic patient records by physicians and other caregivers.

One problem that has not been fully addressed by known automated patient record systems involves caregiver work flow. The types of interactions that caregivers have with patients vary widely from hour to hour and from office to office. In some clinical environments, it is common for several caregivers to interact with a patient during a single visit. Similarly, it is common for a single caregiver to need to access several patient records at nearly the same time.

Due to data integrity concerns (e.g., that a patient record not be open for modification by two users at the same time), it can be confusing and difficult using existing systems to allow multiple caregivers to access information for the same patient or to access information for multiple patients at nearly the same time.

It has also been found that existing systems suffer certain inefficiencies as people in different positions access patient records. For example, a doctor may enter diagnosis information in one format, but insurance requirements may call for an administrator to enter redundant information in a different format.

Therefore, it would be advantageous if an improved patient medical record system and process could provide efficient workflow management by facilitating multiple caregiver access, multiple patient record access, and automatic formatting of diagnostic information.

No known solution adequately addresses these needs in a simple, flexible, robust, and inexpensive manner.

SUMMARY OF THE INVENTION

In accordance with the present invention, a patient record system (100) includes a first caregiver's terminal (110), a second caregiver's terminal (112), and a patient record database with patient data coupled to the first and second terminals and selectively providing access to the patient data from one of the first and second terminals responsive to a predetermined set of access rules.

Further in accordance with the present invention, the predetermined set of rules includes a rule that access to a predetermined portion of the patient data by a first caregiver is terminated before access to the same predetermined portion by a second caregiver is allowed.

Still further in accordance with the present invention, the predetermined set of rules includes a rule arbitrating access to a portion of the patient data when more than one caregiver seeks access to the portion of the patient data.

In yet another aspect of the invention, a patient record system includes a patient chart workflow subsystem configured to allow a caregiver to engage in a first patient encounter corresponding to a first patient while also engaging in a second patient encounter corresponding to a second patient.

In still another aspect of the invention, the patient chart workflow subsystem is configured to allow a caregiver to open encounters for a plurality of patients upon commencing a round of activities.

In another aspect of the invention, a method of maintaining a patient record includes providing a first caregiver with a terminal, providing a second caregiver with a terminal, and selectively permitting the first and second caregivers, using the terminals, to access patient data from a patient record database according to a predetermined set of access rules.

In still another aspect of the invention, a method of maintaining a patient record includes selectively permitting a first caregiver and a second caregiver, using a terminal, to access patient data from a patient record database according to a predetermined set of access rules.

The features and advantages described in the specification are not all-inclusive, and particularly, many additional features and advantages will be apparent to one of ordinary skill in the art in view of the drawings, specification, and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

DETAILED DESCRIPTION OF THE DRAWINGS

The figures depict a preferred embodiment of the present invention for purposes of illustration only. One skilled in the art will readily recognize from the following discussion that alternative embodiments of the structures and methods illustrated herein may be employed without departing from the principles of the invention described herein.

Figure 1:
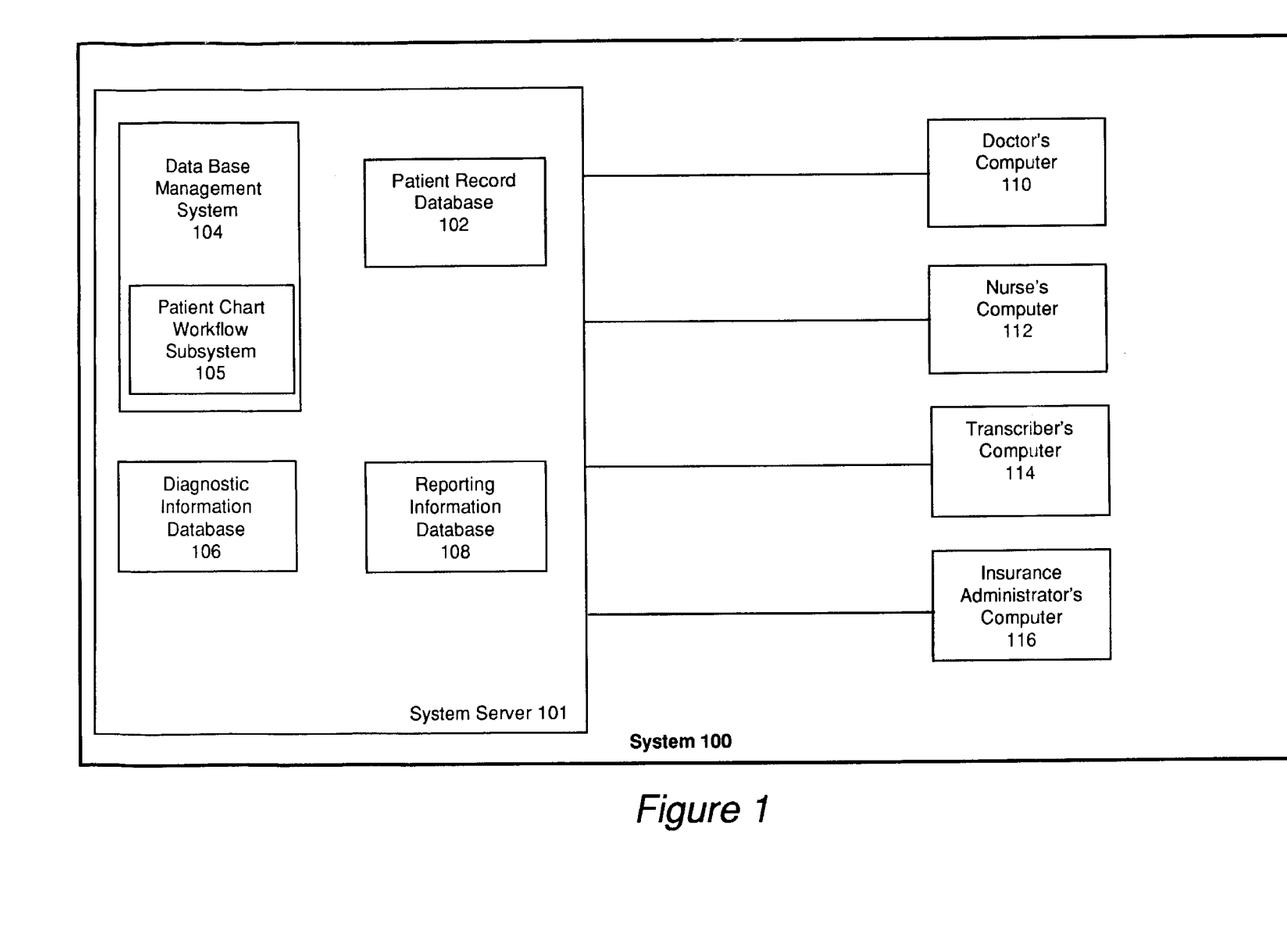
FIG. 1 is a block diagram of a patient record system in accordance with the present invention.

Referring now to FIG. 1, there is shown a patient record system 100 in accordance with the present invention. System 100 includes a patient record database 102, a database management system 104 with a patient chart workflow subsystem 105, a diagnostic information database 106, a reporting information database 108, and user computers 110, 112, 114, 116. In FIG. 1, four separate types of user computers are illustrated: a doctor's computer 110, a nurse's computer 112, a transcriber's computer 114, and an insurance administrator's computer 116.

It should be recognized that as system 100 is intended to provide a generalized medical record in a variety of clinical settings, the number and types of user computers, e.g., 110, will vary with each application. For instance, a practice having five examining rooms, three doctor's offices and two nurse/administrators may have ten terminals: five doctor's computers 110 in the examining rooms, three doctor's computers 110 in the doctors' offices, and two nurse's/ administrator's computers 112, 114 at the nurses' stations. It should also be recognized that system 100 may be implemented using any appropriate computer for each user computer, e.g., 110. For example, the nurse's computer 112 may be a standard desktop personal computer, while the doctor's computer 110 may be a notebook-style computer or personal digital assistant-type computer. Computers 110, 112, 114, 116 are sometimes referred to herein as terminals, as such computers are used primarily for input and output of data. In a preferred embodiment, personal computers are used to implement such terminals. It should be recognized that there may be applications for alternate embodiments in which such terminals may be implemented by devices other than personal computers, such as client workstations, personal digital assistants, or even possibly terminals that do not function as standalone independent computers at all, but rely in part on other equipment connected by a network for their operation.

In operation, system 100 permits any of several caregivers to enter and retrieve data for a patient's medical record. In a typical "intake" situation, an administrator, through administrator's computer 116, may input new patient information such as name, address, and insurance identification data. A nurse 112 may take the patient's vital signs observed during an office visit and enter them into system 100 using nurse's computer 112. A doctor examining the patient may enter the results of the examination, or a diagnosis from the patient's chief complaint, using doctor's computer 110. In some cases, the doctor dictates a detailed description of the encounter with the patient using conventional dictation apparatus, and this dictation is later entered as text into system 100 by a transcriber operating a transcriber's computer 114. After an office visit, the insurance administrator typically processes insurance information pertaining to the visit using computer 116. In a preferred embodiment, system 100 includes a conventional interface with insurance processing programs operating on the insurance administrator's computer 116 to allow the insurance administrator to use information from system 100 in performing insurance-related data processing.

Information used by system 100 takes a variety of forms. Patient-specific information includes patient identification information, patient medical history information, patient visit records, and the like. Information of this sort is stored in patient record database 102.

System 100 also provides medical information not specific to a particular patient that a doctor may use in diagnosing a patient's complaint or for other purposes. For instance, system 100 provides a listing of commonly encountered diagnoses, coupled with links to pertinent related symptom and examination information. This information is stored in a diagnostic information database 106. In a preferred embodiment, this information includes the SNOMED database of diagnostic terms, provided commercially by the American College of Pathologists.

System 100 further provides administrative information not specific to a particular patient that a clinic may use, e.g., for purposes of generating insurance reimbursement requests. This information is stored in a reporting information database 108. In a preferred embodiment, this information includes the ICD-9 database of medical diagnostic codes that are typically used for insurance reporting purposes.

System 100 provides correspondence between diagnostic information from diagnostic information database 106 and administrative information accessed through reporting information database 108. Specifically, in a preferred embodiment, each item of diagnostic information from diagnostic information database 106 is mapped to a corresponding ICD-9 code that is recorded along with the item of diagnostic information. By providing the corresponding ICD-9 code for each diagnostic entry, a caregiver such as a doctor need only enter in the patient record once, during an encounter with a patient, a diagnosis in conventional form for that record to include the ICD-9 code that will be used for insurance reporting purposes with respect to that encounter.

As a specific example, if a doctor selects from diagnostic information database 106 an entry for "acute bronchitis," there is a predetermined correspondence between that entry and an entry from the reporting information database 108. In a preferred embodiment, the corresponding entry for acute bronchitis is the number 466.0, the ICD-9 code corresponding to the diagnosis of acute bronchitis. Thus, when an administrator operating administrator's computer 116 performs administrative data processing for this encounter, the administrator will automatically have presented not only the doctor's diagnosis, but the ICD-9 code corresponding to the diagnosis. In a preferred embodiment, the correspondences between diagnosis entries and ICD-9 codes is predetermined manually and the ICD-9 codes are stored as text along with each diagnostic entry. Accordingly, in a preferred embodiment the diagnostic information database 106 and the reporting information database 108 are implemented together as a single database. In alternative embodiments, the correspondence could be determined, either statically or dynamically, in numerous other ways, for instance by using an expert system-based mapping processor that dynamically selects entries in reporting information database 108 to correspond with entries in diagnostic information database 106.

A database management system 104 coordinates and facilitates movement of data into and among patient record database 102, diagnostic information database 106, and reporting information database 108. In a preferred embodiment, the ORACLE database management system is used for database management system 104.

In a preferred embodiment, components 102, 104, and 106–108 are implemented as a system server 101 using a conventional NT- or Unix-capable server-class computer interconnected with user computers 110, 112, 114, 116, which are configured as client computers.

Both the direct caregivers, such as doctors and nurses, and indirect caregivers, such as insurance administrators and transcribers, have need to access a patient's record at various times. As is evident from the above description, the workflow of typical patient care may call for one caregiver to seek access to information for a particular patient at a time when another caregiver also seeks access to information for that patient.

System 100 manages the flow of patient information during an encounter in a number of ways. System 100 allows multiple caregivers to record information for the same patient visit. System 100 displays all patient information recorded during a visit, regardless of which caregiver recorded the information. System 100 maintains the integrity of patient information that is recorded by each caregiver. System 100 provides a vehicle for a patient's chart to be sent from one caregiver to another.

Figure 2:
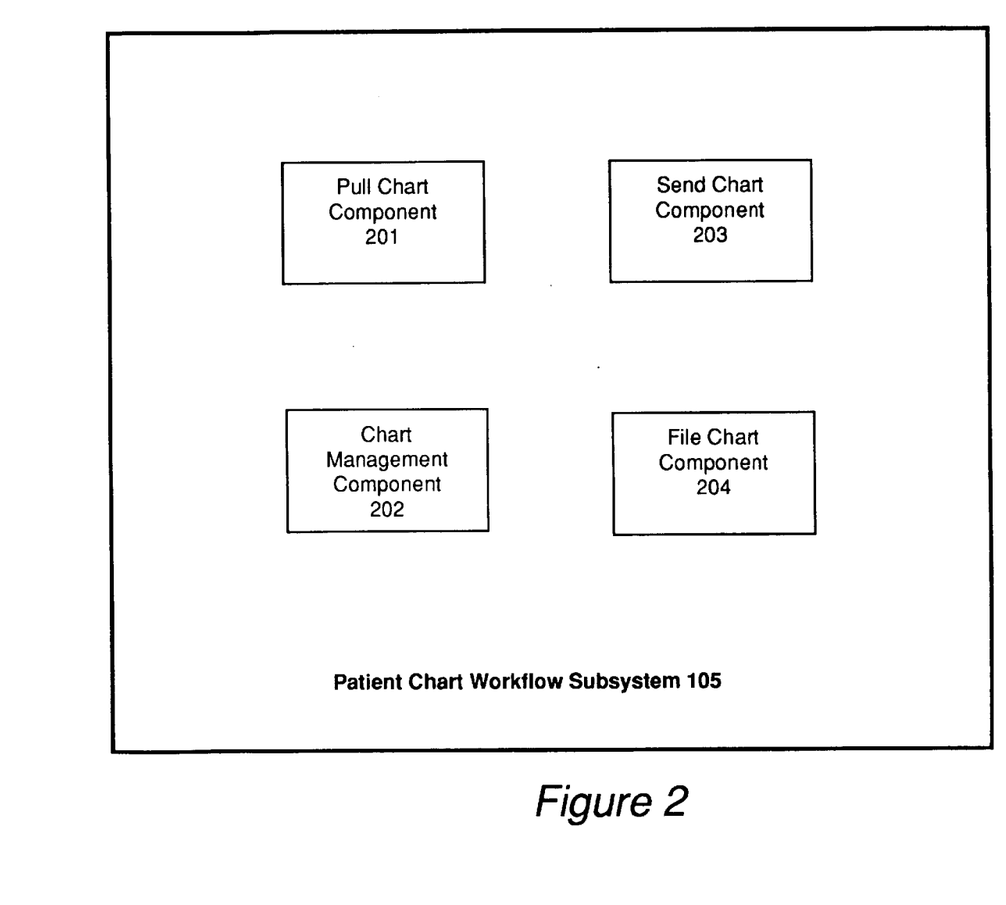
FIG. 2 is a block diagram of the patient chart workflow subsystem illustrated in FIG. 1.

To provide these features, database management system 104 includes a patient chart workflow subsystem 105. Referring now also to FIG. 2, patient chart workflow subsystem 105 includes a pull chart component 201, a chart management component 202, a send chart component 203, and a file chart component 204. Before discussing these components in detail, it will be helpful to provide the following list of terminology:

Chart: A patient's medical record.

Chart List: A list of patients' charts that have been pulled by a caregiver and not yet filed or sent.

Contact: A specific interaction with the patient, or function performed against the patient's chart (e.g., obtaining vital signs, entering chief complaints, recording history of present illness, conducting a physical examination, reviewing medications, reviewing laboratory results). As used herein, a contact is performed by a single caregiver.

Contact Data: The clinical information in a patient's chart that is being recorded for the encounter in progress.

Encounter: Any interaction with a patient's chart (e.g., office visit, phone visit, chart review, medication refill, consultation). An encounter comprises one or more contacts, performed by one or more caregivers.

Preferred Caregiver: The physician who is primarily responsible for the patient's care, also known as the primary caregiver.

Summary Data: The demographic and historical information in the patient's chart that has been recorded during previous encounters. Also included in the category of information are patient reminders, patient orders, and patient laboratory tests.

Patient workflow subsystem 105 enforces predetermined rules for accessing a patient's chart and manages who can pull such charts, as well as under what conditions they can be pulled. The predetermined rules include:

1. Each encounter is considered to be a unique event that can have multiple contacts associated with it. In one embodiment, a unique encounter code is used as a database key to an encounter table that records and manages each encounter.

2. A contact is considered to be a unique event within an encounter. In one embodiment, a unique contact code, together with the corresponding encounter code, are used as a database key to a contact table that records and manages each contact.

3. A new contact is started each time a caregiver pulls a patient's chart, unless the patient's chart has already been pulled by that caregiver.

4. A user interface screen for a new contact displays all the data entered during previous contacts for the same encounter.

5. Only one caregiver at a time is allowed to update patient contact data. Any attempt by one caregiver to update a contact being updated by another results in a message that the contact is already in the process of being updated.

6. When one caregiver begins to record patient contact data after another caregiver has recorded patient contact data for a new contact during the same encounter, a user interface message asks the new caregiver whether that caregiver wants to assume control of the patient's chart. By keeping track of chart "ownership," all caregivers know who is responsible for any particular chart at any particular time.

7. Data from a contact are saved in patient record database 102 whenever a user navigates from one type of contact data (e.g., vital signs) to another (e.g., chief complaint), sends the patient's chart to another caregiver, locks the system (indicating that the user will be away from the user's computer, e.g., 112, for some period of time), exits the program, or views another patient's chart.

8. A contact is considered to be complete whenever the caregiver "files" the patient's chart in patient record database 102, sends the patient's chart to another caregiver, locks the system, exits the program, or views another patient's chart.

9. An encounter is considered complete when the patient's chart is "signed." A chart is signed in system 100 by a doctor saving in patient record database 102 a file providing a History and Physical (H&P) report for the encounter. Whenever contact data have been recorded during an encounter, system 100 requires that the patient's chart be so signed. If no contact data have been entered, such as when a chart is opened for administrative updates or laboratory review, the patient's chart can be filed without saving the H&P report.

10. In a preferred embodiment, until an encounter is saved, all data for that encounter may be modified. Some applications may have data integrity requirements that preclude modification of any data once entered, and an alternate embodiment for use with such an application does not allow such modification of data.

In a preferred embodiment, components 201–204 are implemented by software programs operating as described herein. It should be recognized that other implementations, such as dedicated circuitry, could also be used to implement some or all of the functions of components 201–204.

Pull Chart component 201 manages users' ability to pull patient charts based on patient privacy information and based upon application security levels of a particular caregiver.

Figure 3:
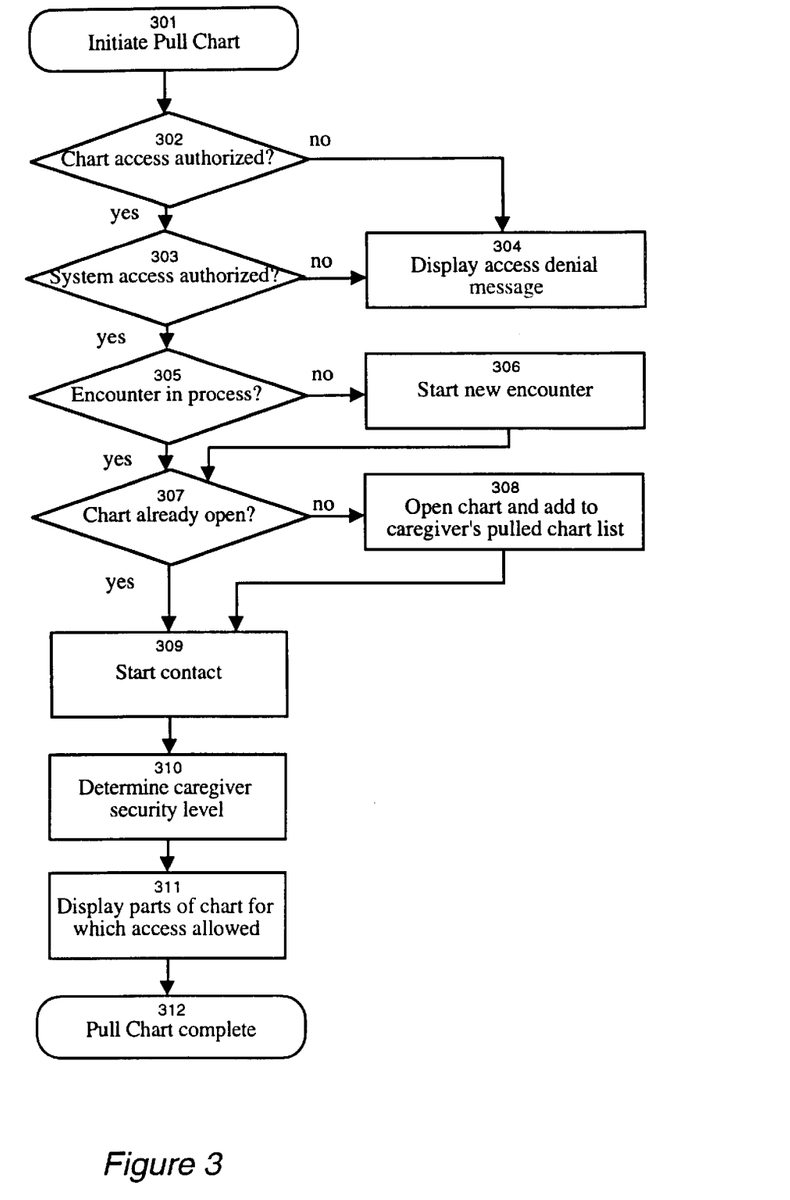
FIG. 3 is a flow diagram of the operation of a pull chart component of a patient chart workflow subsystem in accordance with the present invention.

Referring now also to FIG. 3, when a user of system 100 requests to see a patient chart, processing is initiated 301 for pull chart component 201. First, a check 302 is made to see whether the caregiver is authorized to have any chart access. If so, a check 303 is made to see whether the caregiver is authorized user of system 100. If either check is negative, an access denial message is displayed 304 and the pull chart component 201 terminates. Otherwise, a check 305 is made to see whether an encounter is already in process for the patient. If not, an encounter is started 306.

In either event, a check 307 is then made to see whether a chart is already open on the caregiver's computer, e.g., 110, for this encounter. If so, a contact is started. If not, a chart is opened and added 308 to a list of pulled charts for that caregiver. A contact is then started 309. A determination 310 is made as to the caregiver's security level, and the parts of the patient chart for which access is allowed are then made available for display 311. At this point the pull chart component 201 is complete 312.

In some instances, a patient may have a particular sensitivity to privacy and there may be specific information on which caregivers are authorized to review particular portions of the patient's record. In other cases, there may be no specific privacy instructions, in which case the inquiry will simply be whether the caregiver requesting to pull the chart is authorized to view any patients' charts. Also in a preferred embodiment, a facility is provided for a level of security in which all caregivers authorized to view any patient data may pull a chart, but must always enter a reason for pulling the chart. Still another facility provided in a preferred embodiment allows a preferred provider, someone who is defined as being in the preferred provider's group, or someone on a list of referrals from the preferred provider to have access to some or all of the patient information. The preferred embodiment also provides a feature whereby a preferred provider may have sufficient privileges to override a privacy status, such as one that may have been set by another caregiver.

If it is determined that full access is allowed, the entire chart is accessible for display to the caregiver. In a preferred embodiment, a patient face sheet screen of data is displayed first. If the caregiver is not determined to have full access, the parts of the chart for which access is allowed are accessible for display to the caregiver. In some instances, the caregiver may only have available patient name, address, and billing information; in others, some laboratory or examination results but not doctors' comments may be accessible.

It should be recognized that the processing described above in connection with FIG. 3 may be implemented in various ways. In one embodiment, access levels, encounters and contacts are referenced and maintained using rows of tables or similar conventional data structures. It should also be recognized that numerous variations on the processing described in connection with FIG. 3 could also be used.

In a preferred embodiment, the pull chart component 201 may be selected as a user interface button and menu choice from a variety of display screens on a user computer, e.g., 112. It should be recognized that numerous other ways of implementing the pull chart component 201 could also be used, for instance a dedicated key on a keyboard.

In operation, a caregiver who is a doctor may use system 100 by opening patient encounters for all of the patients who are scheduled to be examined on the doctor's upcoming rounds. The doctor may choose to close these encounters one by one as patients are examined, or may leave all of them open until the doctor's rounds are completed and the doctor can enter further comments and notes for each of the patients examined during the rounds. Used in this manner, system 100 allows a doctor to be called away from one patient to care for another for a brief period of time, and then to return to the first patient without having to first close the first patient encounter, open the second patient encounter, close it, and then start a new encounter for the first patient again.

In a preferred embodiment, users may lock their computers, e.g., 112, by a keystroke sequence to ensure that no passers-by attempt to review patient information while the user is away from the computer. If a chart has been pulled by a caregiver who subsequently locks his or her computer, a new pull chart process is initiated when the computer is again unlocked. In such a situation, the user is returned to the portion of the chart that was being viewed when the computer was locked. In some instances, a particular computer may be locked by one caregiver and unlocked by another. If the new caregiver is not authorized with respect to that chart, it is not displayed. If the new caregiver is authorized, the chart is pulled for the new caregiver.

In some instances, a caregiver may open one patient chart without closing another first. As a result, a chart may not appear on any caregiver's computer screen, but will still remain open in the sense that it was never signed. This will also happen when a caregiver exits one or more of the programs used in implementing system 100, or when system 100 stops operating due to a computer system crash while a patent contact is in process. To account for such possible situations, patient workflow subsystem 105 maintains a record of all such open patient charts, and provides each caregiver with an indication of all open patient charts for which that care giver remains responsible. The number of open encounters for a caregiver is indicated on the caregiver's computer, e.g., 110. In one embodiment, this is achieved by using a numeral next to an icon representing a stack of open patient charts. It should be recognized that numerous other user interfaces could be used to provide caregivers with visual or other indication of the encounters they currently have open.

In a preferred embodiment, there is no limit to the number of caregivers who can pull a patient's chart. Each request to open a patient chart starts a patient contact with the chart status set to that of a readable copy, as discussed below. A caregiver's access to patient summary and contact information is restricted only by the security controls discussed herein. Even if a caregiver is denied access to a chart because it is being updated, the caregiver still has access to information for that patient from previous encounters.

Once a caregiver requests access to patient contact information, chart management component 202 is automatically invoked.

Turning now to chart management component 202, once a caregiver pulls a patient's chart, chart management component 202 monitors the status of that chart. This component keeps track of whether contact data have been recorded for this contact and which caregiver, if any, is in the process or recording contact data. This component also manages control of which caregiver can update the patient contact data and how the chart may be filed once the contact is complete.

In a preferred embodiment, the overall status of a chart is tracked by characterizing a copy of the chart as being in one of three modes. A readable copy of a chart is one in which the caregiver has not entered contact data, for instance entering data on a patient summary screen. A writeable copy of a chart is one in which a caregiver has entered contact data, such as by entering data using a patient contact screen. A locked copy of a chart is one in which contact data is currently being entered by a caregiver, thus locking other caregivers out of access to the patient contact screens.

If a caregiver has a readable copy of a patient's chart, the caregiver can file the chart without being required to save an H&P report even if contact data have been entered for the encounter by another caregiver. For example, a nurse can pull a chart, update demographic information and file the chart immediately even though physical examination recordings are being simultaneously recorded by another caregiver.

If a caregiver has a writeable copy of a patient's chart, the caregiver can file the chart but first is required to save an H&P report for that encounter, because contact data have been entered. When a second caregiver takes over a writeable copy from another caregiver, system 100 displays a message asking the second caregiver if he or she wants to take over the chart from the first caregiver. If so, then the writeable copy is transferred to the second caregiver and becomes a locked copy. Thus, for example, a first caregiver may record contact data and then move to a summary screen before transferring a chart to a second caregiver. Upon receiving the chart, the second caregiver moves to a contact data screen and thereby causes the chart to become a locked copy.

As suggested earlier, when a contact is in read only mode and no data have been recorded for the contact, the patient's chart can be filed from any user's computer, e.g., 114, without being signed. This permits a caregiver to open a patient's chart to review and update demographics and patient summary information without interrupting another caregiver who may be recording contact information for a patient encounter. For example, a nurse operating nurse's computer 112 has the ability to update test result information for a patient while a physician operating doctor's computer 110 continues to report findings from an ongoing physical examination.

When contact data have already been recorded, the chart will not be removed from a caregiver's computer display until it is signed (by saving an H&P report as earlier described) or sent to another caregiver. This ensures that the patient's H&P report will be reviewed before the patient's chart is closed, thus helping to maintain the integrity between the contact data recorded during an encounter and the final H&P report summarizing the encounter.

The update mode indicates that information for a contact is being recorded by a caregiver. All other caregivers who attempt to pull the patient's chart are restricted from entering contact data, and as a further reminder a unique identifier, for instance the phrase "(IN USE)," is displayed next to the patient's name in the overall listing of patients for whom charts are available. This ensures that the integrity of the information entered during each contact is maintained, and allows system 100 to ensure that when each caregiver is examining patient contact information, the system can display the most up-to-date information on which decisions can be made.

The send chart component 203 permits one caregiver to send a message to another concerning a particular patient, and to attach the patient's chart to that message. The recipient of the chart message must be an authorized caregiver and must have authorization to pull the patient's chart, as well as have the requisite access to see the patient summary or patient contact information to which the message may pertain.

When a caregiver invokes the send chart component 203, that caregiver's contact with that patient ends, the patient's chart is filed from that caregiver's computer, and the patient name is removed from a display of pulled charts on the caregiver's computer.

Sending a chart from one caregiver to another does not end the current patient encounter. This provides a mechanism for a caregiver to transfer a patient's chart to another caregiver to facilitate the recording of additional contact data during an encounter.

In order to keep track of such charts, for instance to make sure that the encounter ultimately gets saved, a message is created when a chart is sent from one caregiver to another, and the message and the corresponding patient's chart are associated with one another. The new caregiver is presented with the message and is required to pull the chart.

If the caregiver is sent a writeable copy of a chart, the caregiver is called upon to either pull the patient's chart or forward it to another caregiver. Conventional logic is used to prevent a caregiver from removing the message until the chart is pulled. Conventional logic also checks to determine whether the target caregiver has permission to view the chart to be sent; if not, the request to send the chart to that caregiver is denied.

The file chart component 204 is used to end a patient contact and save a patient encounter. Whether an H&P report must be saved when a chart is filed depends upon whether contact data was entered during the encounter. If no contact data has been recorded during a contact, the patient's chart can be filed (i.e., the contact ended and the encounter closed) without saving an H&P report. When contact data have been recorded during that contact, executing the file chart component 204 will open a display window allowing the caregiver to produce an H&P report. If the caregiver has the proper level of security clearance, the caregiver can save the H&P report (thereby ending the contact and closing the encounter) and file the patient's chart from the caregiver's computer. If the caregiver does not have sufficient security clearance, the caregiver can end a contact by using the send chart component to transfer the chart to a caregiver who has the authority to save the H&P report.

When an encounter has only one contact, filing the patient's chart (thereby ending the contact) also serves to end the current encounter.

Whenever a chart is filed, either along with saving an encounter or not, the patient's name is removed from the display of open charts on the caregiver's computer.

A patient's chart that is open on one caregiver's computer, e.g., 110, may simultaneously be opened on another caregiver's computer, e.g., 112, after the first caregiver has saved the H&P report for that patient encounter. Thus, a physician may complete work on a patient encounter but the contact may remain open so that a nurse may continue to update patient information such as lab results. The nurse is provided with access to such patient summary data but not to patient data relating to the concluded encounter. Once the nurse's work is complete, the nurse files the patient chart (i.e., ends the contact), without the need for any further H&P report.

In a preferred embodiment, a cancel contact user interface selection is also available to a caregiver. When executed, the cancel contact selection deletes the various data structures created as a result of the current contact, and all other entries corresponding to that contact are deleted.

A caregiver request to switch from display of a first chart to display of a second chart is implemented by relinquishing control of the first chart so that it is available for use by other caregivers, if such caregiver had control of the first chart to begin with; ending the contact corresponding to the first chart, and invoking the pull chart component 201 to obtain access to the second chart.

From the above description, it will be apparent that the invention disclosed herein provides a novel and advantageous medical record management system and process with workflow management features. The foregoing discussion discloses and describes merely exemplary methods and embodiments of the present invention. As will be understood by those familiar with the art, the invention may be embodied in other specific forms without departing from the spirit or essential characteristics thereof. Accordingly, the disclosure of the present invention is intended to be illustrative, but not limiting, of the scope of the invention, which is set forth in the following claims.

What is claimed is:

1. A patient record system for recording and maintaining medical information for a patient, comprising:

a first caregiver's terminal to allow a first caregiver to access the patient record system;

a second caregiver's terminal to allow a second caregiver to access the patient record system;

a patient record database having patient data, the patient record database being coupled to said first and second caregivers' terminals, the patient record database providing a first contact portion corresponding to access by the first caregiver to the patient record system and a second contact portion corresponding to access by the second caregiver to the patient record system, the patient record database selectively providing access to the patient data from one of the first and second caregiver's terminals responsive to a predetermined set of access rules.

2. A patient record system as in claim 1, wherein the predetermined set of access rules includes a rule selectively permitting access to a portion of the patient data responsive to the first caregiver having authorization for access to said portion of the patient data and responsive to the portion of data not being accessed by another caregiver.

3. A system as in claim 1, further comprising a patient chart workflow subsystem operatively coupled to said patient record database and said first and second caregiver's terminals, the patient chart workflow subsystem configured to allow the first caregiver to engage in a first patient encounter corresponding to a first patient while engaging in a second patient encounter corresponding to a second patient.

4. A system as in claim 3, wherein the patient chart workflow subsystem is further configured to allow said first caregiver to open a plurality of encounters for a plurality of patients, upon commencing a round of activities.

5. A method of maintaining a patient record, comprising:

providing a first caregiver with a terminal;

providing a second caregiver with a terminal; and selectively permitting the first and second caregivers, using said terminals, to access portions of patient data from a patient record database according to a predetermined set of access rules, the patient record database providing a first contact portion corresponding to access by the first caregiver to the patient record system and a second contact portion corresponding to access by the second caregiver to the patient record system.

6. A method as in claim 5, wherein the predetermined set of rules includes a rule selectively permitting access to said portions of the patient data when more than one caregiver seeks access to said portions of the patient data and responsive to caregiver authorization to access said portions of the patient data.

7. A method of maintaining patient records, comprising:

providing a first caregiver with a first terminal;

providing a second caregiver with a second terminal;

creating encounter records for a plurality of patients; and selectively permitting the first and second caregivers, using said first and second terminals, to access portions of patient data corresponding to a subset of said plurality of patients from a patient record database according to a predetermined set of access rules, the encounter records including a first contact record corresponding to access by the first caregiver to the patient records and a second contact record corresponding to access by the second caregiver to the patient records.

8. A method as in claim 7, wherein said predetermined set of rules includes a rule permitting said first caregiver to access said portions for all of said plurality of patients for whom said first caregiver is authorized, other than ones of said patients for whom said second caregiver is accessing corresponding portions of said patient data.

9. A method as in claim 7, further comprising maintaining the patient record in a writeable mode permitting said first caregiver to transfer, to said second caregiver, access to said selected portions.

10. A method as in claim 7, further comprising sending a patient record from said first caregiver performing a first type of processing, to said second caregiver performing a second type of processing.

11. A method as in claim 7, further comprising accessing a second record for a second patient while maintaining said patient record as an open patient chart.

12. A method as in claim 7, further comprising maintaining a list of said subset of patients.

13. A method of maintaining a patient record, comprising:

providing a terminal; and selectively permitting a plurality of caregivers, using said terminal, to access portions of patient data from a patient record database according to a predetermined set of access rules, the patient database providing a plurality of encounter records, each corresponding to interaction with data for a particular patient, the encounter records further including a plurality of contacts, each corresponding to interaction with said data for said particular patient by one of said plurality of caregivers.

14. A method as in claim 13, further comprising:

locking said terminal by a first one of said caregivers; and accessing said portions of patient data by a second one of said caregivers responsive to said second caregiver unlocking said terminal and said second caregiver having access privileges to said portions of patient data.

* * * * *